(12) United States Patent
Banks et al.

(10) Patent No.: US 10,106,849 B2
(45) Date of Patent: Oct. 23, 2018

(54) HIGH THROUGHPUT METHOD OF SCREENING A POPULATION FOR MEMBERS COMPRISING MUTATION(S) IN A TARGET SEQUENCE USING ALIGNMENT-FREE SEQUENCE ANALYSIS

(71) Applicant: Vineland Research and Innovations Centre Inc., Vineland Station (CA)

(72) Inventors: Travis Wilfred Banks, Fonthill (CA); Daryl John Somers, Fenwick (CA)

(73) Assignee: Vineland Research and Innovations Centre Inc., Vineland Station, Ontario (CA)

( * ) Notice: Subject to any disclaimer, the term of this patent is extended or adjusted under 35 U.S.C. 154(b) by 0 days.

(21) Appl. No.: 15/504,211

(22) PCT Filed: Nov. 3, 2016

(86) PCT No.: PCT/CA2016/051277
§ 371 (c)(1),
(2) Date: Feb. 15, 2017

(87) PCT Pub. No.: WO2017/075706
PCT Pub. Date: May 11, 2017

(65) Prior Publication Data
US 2017/0335388 A1    Nov. 23, 2017

(30) Foreign Application Priority Data
Nov. 4, 2015   (CA) .................................... 2911002

(51) Int. Cl.
*C12Q 1/68* (2018.01)
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

2010/0112557 A1\* 5/2010 Tobler ................... C12Q 1/6848
435/5
2015/0073724 A1 3/2015 Ashutosh et al.

FOREIGN PATENT DOCUMENTS

| CA | 2874535 A1 | 9/2014 |
|---|---|---|
| CA | 2911002 A1 | 1/2016 |
| WO | WO-2007/037678 A2 | 4/2007 |
| WO | WO 2007/037678 † | 5/2007 |
| WO | WO-2014/134729 A1 | 9/2014 |

OTHER PUBLICATIONS

Halbritter et al., "High-trhoughtput mutation analysis in patients with a nephronophthisis-associated ciliopathy applying multiplexed barcoded arra-based PCR amplification and nest-generation sequence-ing" 49 Journal of Medical Genetics 756-767 (2012).\*
Arnau et al., "Fast comparison of DNA sequences by oligonucle-otide profiling," BMC Res Notes. 1(5):1-5 (2008).
Bonham-Carter et al., "Alignment-free genetic sequence compari-sons: a review of recent approaches by word analysis," Brief Bioinform. 15(6):890-905 (2013).
Communication Pursuant to Rule 114(2) EPC for European Patent Application No. 16836042.8, dated Jul. 19, 2017 (16 pages).
Rigola et al., "High-throughput detection of induced mutations and natural variation using KeyPoint™ technology," PLoS One. 4(3):e4761, 1-9 (2009).
Nordstrom et al., "Mutation identification by direct comparison of whole-genome sequencing data from mutant and wild-type indi-viduals used k-mers," Nature Biotechnology. 31(4):325-30 (7 pages) (2013).
Office Action for Canadian Patent Application No. 2,911,002, dated May 26, 2016, Banks et al., "High throughput method of screening a population for members comprising mutation(s) in a target sequence using alignment-free sequence analysis," filed Nov. 4, 2015 (7 pages).
Zastrow-Hayes et al., "Southern-by-Sequencing: a robust screening approach for molecular characterization of genetically modified crops," The Plant Genome. 8(1):1-15 (15 pages) (2015).
Lindgreen, "AdapterRemoval: easy cleaning of next-generation sequencing reads," BMC Res Notes. 5:337 (2012) (7 pages).
Missirian et al., "Statistical mutation calling from sequenced over-lapping DNA pools in TILLING experiments," BMC Bioinformat-ics. 12:287 (2011) (10 pages).
Office Action dated Oct. 18, 2017 for European Patent Application No. 14759987.2, Banks et al., "High Throughout Method of Screen-ing a Population for Members Comprising Mutation(s) in a Target Sequence," filed Mar. 6, 2014 (12 pages).
Roche, "454 Sequencing System: Guidelines for Amplicon Experi-mental Design," (2011) (50 pages).

(Continued)

*Primary Examiner* — Nancy J Leith
(74) *Attorney, Agent, or Firm* — Clark & Elbing LLP

(57) ABSTRACT

The present invention provides methods for isolation of a member of a population which has one or more mutation(s) in one or more target sequence(s) in a population. The method may comprise the steps of: (a) pooling genomic DNA isolated from each member of the population in one or more dimensions; (b) amplifying the one or more target sequence(s) in the pooled genomic DNA, wherein optionally the amplification products are pooled; (c) sequencing the amplified products or obtaining the sequence reads for the amplified products, wherein, optionally, sequencing is by pair-end sequencing and further comprises merging the paired-end reads into composite read(s); (d) identifying the mutation(s) based on alignment-free sequence analysis of sequencing data, optionally by k-mer analysis and (e) iden-tifying individual member(s) of the population comprising the one or more identified mutations in the target sequences, optionally by high-resolution DNA melting (HRM).

10 Claims, No Drawings

(56) References Cited

OTHER PUBLICATIONS

Rodrigue et al., "Unlocking short read sequencing for metagenomics," PLoS One. 5(7):e11840 (2010) (9 pages).
Supplementary European Search Report dated Oct. 24, 2017 for European Patent Application No. 16836042.8, Banks et al., "High Throughput Method of Screening a Population for Members Comprising Mutation(s) in a Target Sequence Using Alignment-Free Sequence Analysis," filed Nov. 3, 2016 (5 pages).
Tsai et al., "Discovery of rare mutations in populations: TILLING by sequencing," Plant Physiol. 156(3):1257-68 (2011).
Tsai et al., "Production of a high-efficiency TILLING population through polyploidization," Plant Physiol. 161(4):1604-14 (2013).
International Preliminary Report on Patentability dated May 8, 2018 for International Patent Application No. PCT/CA2016/051277, Banks et al., "High Throughout Method of Screening a Population for Members Comprising Mutation(s) in a Target Sequence Using Alignment-Free Analysis," filed Nov. 3, 2016 (4 pages).
Office Action dated Dec. 19, 2017 for European Patent Application No. 16836042.8, Banks et al., "High Throughout Method of Screening a Population for Members Comprising Mutation(s) in a Target Sequence Using Alignment-Free Analysis," filed Nov. 3, 2016 (10 pages).
Rigola et al., "High-throughput detection of induced mutations and natural variation using KeyPoint (TM) technology," *PLoS One* 4(3): e4761 (2009) (published Mar. 13, 2009), p. 3.†
Van Eijk et al., WO 2007/037678, "High throughput screening of mutagenized populations" (published Apr. 5, 2007), p. 7.†
Nordström et al., "Mutation identification by direct comparison of whole-genome sequencing data from mutant and wild-type individuals using k-mers," *Nature Biotechnology* 31(4): 325-330 Mar. 10, 2013, Supplementary Online Materials, 1-73, and online version, available at https://www.nature.com/nbt/journal/v31/n4/full/nbt.2515.html, p. 14.†
Bonham-Carter et al., "Alignment-free genetic sequence comparisons: a review of recent approaches by word analysis," *Briefings in Bioinformatics* 15(6): 890-905 (published Jul. 31, 2013), p. 18.†
Rodrigue et al. "Unlocking short read sequencing for metagenomics," *PLoS One* 5(7):e11840 (2010) (published Jul. 28, 2010), p. 22.†
Arnau et al. "Fast comparison of DNA sequences by oligonucleotide profiling," *BMC Research Notes* I(5): 1-5 (2008) (published Feb. 28, 2008), p. 24.†
Rigola et al. "High-throughput detection of induced mutations and natural variation using KeyPoint(TM) technology" PLoS ONE 4(3):e4761 (Mar. 13, 2009) 9 pages.†
Nordström et al., "Mutation identification by direct comparison of whole-genome sequencing data from mutant and wild-type individuals using k-mers," Nature Biotechnology 31(4): 325-330 (Mar. 10, 2013) 7 pages.†
Bonham-Carter et al., "Alignment-free genetic sequence comparisons: a review of recent approaches by word analysis," Briefings in Bioinformatics 15(6): 890-905 (Jul. 31, 2013) 16 pages.†
Rodrigue et al. "Unlocking short read sequencing for metagenomics," PLoS One 5(7):e11840 (Jul. 28, 2010) 9 pages.†
Arnau et al. "Fast comparison of DNA sequences by oligonucleotide profiling," BMC Research Notes I(5): 1-5 (Feb. 28, 2008) 5 pages.†

\* cited by examiner
† cited by third party

HIGH THROUGHPUT METHOD OF SCREENING A POPULATION FOR MEMBERS COMPRISING MUTATION(S) IN A TARGET SEQUENCE USING ALIGNMENT-FREE SEQUENCE ANALYSIS

FIELD OF THE INVENTION

The present invention pertains to the field of molecular biology and genetics. In particular, the present invention relates to high-throughput reverse genetic methods of screening for members of a population comprising mutation(s) in one or more target sequence(s) using alignment-free sequence analysis. The invention further provides kits for use with the methods.

BACKGROUND OF THE INVENTION

The global agriculture industry faces many challenges and pressures that are particularly evident in the production of sessile organisms: biotic and abiotic stresses threatening crop yield and quality; increasing labour, water and energy costs; and further constraints imposed by consumer preference. As such, there is great demand to produce crops that are stress tolerant, require little or no input (i.e. reduced use of water, fertilizer, and/or pesticides), and are also appealing to consumers. The possibilities for trait development using traditional breeding are becoming increasingly limited due to a lack of genetic diversity in cultivated plant varieties. Introgression of valuable traits from wild accessions is possible, but this approach might not be feasible if the trait of interest is closely linked to those associated with undesirable traits (Fitzpatrick et al, Plant Cell. 24:395-414). A transgenic approach can be pursued, but genetically-modified organisms, particularly those yielding edible products, are controversial and present entirely new challenges with respect to food safety regulations and consumer acceptance. Mutagenesis is an effective and efficient method to introduce genetic diversity in crop plants (Wang et al, Plant Biotechnology Journal 10:761-772).

Mutagenesis of plants for crop improvement is a technique that has been used for nearly a century. Some of the first reports of human-directed plant mutagenesis come from Lewis Stadler who, in the 1920's, irradiated barley and maize with X-rays and ultraviolet light (Stadler 1932). Chemical mutagenesis was introduced as an alternate technique making use of alkylating reagents such as ethylmethane suphonate (EMS), which disrupts DNA and leads to heritable changes in the genome (Koornneef et al. 1982). There have been many successes in using mutagenesis to develop new traits and new varieties of crops. The International Atomic Energy Agency (IAEA) which is a branch of the United Nations Food and Agriculture Organization (FAO) headquartered in Vienna, Austria provide a database of registered varieties derived from mutagenesis (mv-ga.isea.org). A popular example of a mutant variety is Ruby Red Grape fruit, released in 1970 in Texas, which used irradiation to improve the red colour and colour retention of grapefruit. Also, Golden Promise barley was produced through mutation causing semi-dwarfism, higher yield and salt tolerance (Forster 2001). Both of these varieties have been used extensively to produce modern day varieties of grapefruit and barley.

Alternatives to mutagenesis for inducing changes to the genome have been developed in the last few decades. Methods include using artificial constructs, often hybrids of DNA/RNA with other amino acids or nucleic acids (Sargent et al, Oligonucleotides 21(2):55-75, 2011, KEYBASE® by KeyGenex), to induce genetic changes at a specific location(s). The hybrid molecules are delivered into the cell through biolistics or membrane fusion where they then migrate to the nucleus to affect a change to the genome. The affected cells are then coaxed to grow into full plants. More recently site specific mutagenesis through the use of designer enzyme systems have been developed. Zinc-finger nucleases, transcription activator-like effector nucleases and meganucleases are all specifically designed enzymes that have the ability to cut genomic DNA at a desired location. These enzymes are either expressed in the cell(s) of a plant from a transgene construction introduced to the genome or from an extra-genomic fragment present within the cell. Recently they have been delivered into plant cells as proteins, eliminating the need of introducing foreign DNA into the plant cell. All of these enzymes are able to cut the double-strand DNA of the genome. This activates the cell's DNA repair mechanism which allows the incorporation of a new fragment of DNA through homologous recombination, or the plant closes the break, inducing some kind of change, be it an insertion, deletion or substitution through the process of non-homologous end-joining. More recently a new type of designer nuclease has been developed based on the bacterial immunity mechanism called the CRISPR/Cas system. The main benefit of the CRISPR/Cas system is that an RNA molecule is used to give the complex its genome editing specificity. This is in contrast to all other previous nuclease technologies where genome specificity was achieved by designing custom DNA binding protein domains. With CRISPR/Cas, genome targeting occurs through the complementary pairing of an RNA guide molecule to a target region, so customizing a new nuclease is as easy as designing a new RNA guide sequence. Like previous nucleases, the constructs expressing this system are placed into a cell where it is expressed and modifies the genome.

A genetic screen is used to identify and select for individuals who possess a phenotype of interest in a mutagenized or modified population. Types of genetic screens include forward genetic screens and reverse genetic screens. A forward genetic screen first identifies individuals of a mutant population with a particular phenotype of interest. Once the phenotype has been found, follow-on work is done to identify the underlying genetic change that led to the creation of the new trait. For example, Nordstrom et al. (Nat. Biotech. 31(4):325-331; 2013) utilize k-mers (short, overlapping nucleic acid fragments) in a forward genetic screen to identify mutations by direct comparison of whole-genome sequencing data from mutant and wild-type individuals. A reverse genetic screen, opposite to a forward genetics screen, analyzes the phenotype of an organism following the disruption of a known gene.

Mutagenesis of crop plants was, until recently, exclusively used in a forward genetic screen approach, whereby large mutagenized populations were phenotyped in search of novel traits for crop improvement. This approach is labour intensive, prone to identifying false positives and constrained by what can be measured visually or by high throughput methods.

Because of the labour associated with forward genetic screens, mutagenesis and mutation breeding lost popularity until the prospects of applying molecular biology were considered.

Targeting induced local lesions in genomes (TILLING) is a reverse genetics approach whereby high density, random mutagenesis of populations and single nucleotide polymorphism (SNP) detection techniques are combined to identify plants with valuable mutations (McCallum et al. 2000). High-Resolution DNA Melting (HRM) has been used in TILLING approaches for mutation detection in EMS-treated populations (Gady et al, Plant Methods 5:13), however this approach is labour intensive and expensive.

SNP detection in plants has quickly advanced since 2000 and now it is common to use next generation sequencing (NGS) to discover SNPs in populations of plants (Missirian et al. 2011, Rigola et al. 2009, Tsai et al., 2011).

Next generation DNA sequencing (NGS) is an appealing tool to identify mutations in populations of individuals. The rapidly falling price, ever increasing throughput and complete DNA characterization of the sequencing targets has drawn researchers to investigate NGS as a TILLING tool (Rigola et al, PLoS One 4:e4761; Tsai et al, Plant Pysiology 156:1257-1268). However, due to the intrinsic error-rate of NGS technologies it is difficult to discern mutation from sequencing mistakes in pools of thousands of individuals. Illumina sequencing technology produces a base-calling error almost twice every 1000 bases sequenced (Minoche et al, Genome Biology 12:R112). In an effort to differentiate errors from mutation, researchers have created multi-dimensional pooling strategies combined with DNA barcoding to sequence members of a population in multiple, independent reactions. Individuals harbouring a mutation are then determined by pool deconvolution using the barcodes (Rigola et al, PLoS One 4:e4761; Missirian et al, BMC Bioinformatics 12:287; WO2007037678 to KeyGene N.V.). Strategies which utilize composite reads to reduce error rate have also been developed (WO2014/134729).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide high-throughput methods of screening a population for members comprising mutation(s) in one or more target sequence(s) using alignment-free sequence analysis. In accordance with an aspect of the present invention, there is provided a method for identifying member(s) of a population comprising one or more mutation(s) in one or more target sequence(s), wherein each member of said population is distinct, said method comprising the steps of: (a) pooling genomic DNA isolated from each member of the population in one or more dimensions; (b) amplifying the one or more target sequence(s) in the pooled genomic DNA; (c) sequencing the amplified products to produce sequence read(s) for the amplified products; (d) identifying the mutation(s) based on k-mer analysis of the sequence read(s) of (c); wherein said k-mer analysis comprises (i) decomposing said sequence read(s) into k-mers; (ii) determining the number of occurrences of each of said k-mers from said decomposed sequencing read(s); (iii) determining a wild-type count and a mutant count for the target sequence k-mers using reference sequence(s) to identify all possible k-mers containing a particular base of the reference or target sequence, wherein, for each base in said reference sequence(s), said wild-type count is determined by determining frequency of all k-mers identified from said reference sequence(s) which include said base in said target sequence k-mers from said decomposed sequencing read(s); wherein, for each base in said reference sequence(s), said mutant count is determined by changing said base in said reference sequence(s) to a different base to produce an altered reference sequence(s), identifying all k-mers containing the changed base, and determining frequency of said k-mers containing the changed base in said target sequence k-mers from said decomposed sequencing read(s); (iv) identifying a mutation of said base in the target sequence(s); wherein a ratio of mutant count to wild-type count for said base that is significantly different than the ratio of mutant to wild-type counts for all other bases in said target sequence(s) is indicative of a mutation of said base in said target sequence(s); and (e) identifying individual member(s) of the population comprising the one or more identified mutation (s) in the target sequences.

In certain embodiments, the sequencing is by pair-end sequencing and further comprises merging the paired-end reads into composite read(s). In certain embodiments, the step of amplifying comprises amplifying more than one sample of the pooled genomic DNA, and pooling amplification products from each sample to create pool(s) of amplification products. In certain embodiments, the sequencing is conducted by a third party. In certain embodiments, the population is mutagenized by mutation-inducing chemicals, ionizing radiation, targeted nucleotide exchange or region targeted mutagenesis. In certain embodiments, identifying member(s) of the population comprises one or more of the identified mutations in the target sequence(s) is by high-resolution DNA melting (HRM). In certain embodiments, the method further comprises, after the step of identifying individual member(s) of the population comprising the one or more identified mutations in the target sequences, conducting phenotypic analysis of said individual member(s) comprising the one or more identified mutations in the target sequences.

In accordance with another aspect of the present invention, there is provided a method for identifying one or more mutation(s) in one or more target sequence(s), said method comprising the steps of: (a) decomposing sequence read(s) of the one or more target sequence(s) into k-mers; (b) determining the number of occurrences of each of said k-mers from said decomposed sequencing read(s); (c) determining a wild-type count and a mutant count for the target sequence k-mers using reference sequence(s) to identify all possible k-mers containing a particular base of the reference or target sequence, wherein, for each base in said reference sequence(s), said wild-type count is determined by determining frequency of all k-mers identified from said reference sequence(s) which include said base in said target sequence k-mers from said decomposed sequencing read(s); wherein, for each base in said reference sequence(s), said mutant count is determined by changing said base in said reference sequence(s) to a different base to produce an altered reference sequence(s), identifying all k-mers containing the changed base, and determining frequency of said k-mers containing the changed base in said target sequence k-mers from said decomposed sequencing read(s); and (d) identifying a mutation of said base in the target sequence(s); wherein a ratio of mutant count to wild-type count for said base that is significantly different than the ratio of mutant to wild-type counts for all other bases in said target sequence(s) is indicative of a mutation of said base in said target sequence(s).

In certain embodiments, the population is a population of plants. In specific embodiments, the plant is a grain crop, oilseed crop, fruit crop, vegetable crop, a biofuel crop, an ornamental plant, a flowering plant, an annual plant or a perennial plant. In more specific embodiments, the plant is selected from the group consisting of petunia, tomato, pepper, lettuce, potato, onion, carrot, broccoli, celery, pea, spinach, impatiens, cucumber, rose, sweet potato, fruit trees, eggplant, okra, corn, soybean, canola, wheat, oat, rice, soghum, cotton and barley.

DETAILED DESCRIPTION OF THE INVENTION

Described herewith is a reverse genetics method for identification of a mutation(s) in one or more target sequences and, in some embodiments, isolation of a member of a population which has mutation(s) in one or more target sequence(s). The method utilizes an alignment-free methodology to identify mutations in one or more target sequences. In specific embodiments, the method utilizes short, overlapping fragments (k-mers, also referred to as kmers) to identify polymorphic loci (such as mutations).
Target Sequence The candidate target sequence(s) may be a previously identified target sequence(s) or may be identified through analysis of the scientific literature and/or experimentation. Typically, a target sequence is a region of a gene that a mutation would have an effect. For example, a worker skilled in the art would readily appreciate that mutations in non-coding sequences, such as introns, may have little or no effect. Such a worker would further appreciate that mutations in conserved coding regions of genes have an increased likelihood of having an effect. Typically, a target sequence is greater than 1000 bases in length to facilitate fragmentation during sequencing library preparation. In cases where the target sequence is greater than the longest PCR amplicon possible with the chosen DNA polymerase, multiple PCR amplicons are created. In certain embodiments where multiple PCR amplicons are necessary, the PCR amplicons may have a 200 bp or more overlap.

In embodiments in which multiple target sequences are examined, each of the target sequences may be in the same or different genes. For example, in embodiments where two target sequences are examined, both target sequences may be in the same gene or the first target sequence may be in a first gene and the second target sequence may be in a second gene. Accordingly, in certain embodiments, one or more genes are screened for mutations. In certain embodiments, two or more genes are screened for mutations. In certain embodiments, three or more genes are screened for mutations.
Population The population from which the genomic DNA is isolated may be a non-mutagenized population, mutagenized organisms and/or the progeny thereof (including but not limited to plants or cells). The population may be plants, cells or animals such as Drosphila or mice. The plants may be, for example, a grain crop, oilseed crop, fruit crop, vegetable crop, a biofuel crop, an ornamental plant, a flowering plant, an annual plant or a perennial plant. Examples of plants include but are not limited to petunia, tomato (Solanum lycopersicum), pepper (Capsicum annuum), lettuce, potato, onion, carrot, broccoli, celery, pea, spinach, impatiens, cucumber, rose, sweet potato, apple and other fruit trees (such as pear, peach, nectarine, plum), eggplant, okra, corn, soybean, canola, wheat, oat, rice, soghum, cotton and barley. In certain embodiments, the population is a variety of annuals. In specific embodiments, the population is a population of tomatoes. In other specific embodiments, the population is a population of peppers.

A worker skilled in the art would readily appreciate that mutations may occur spontaneously in a population or the population may be mutagenesized by chemical means or physical means. For example, a worker skilled in the art would readily appreciate that ethylmethane sulfonate (EMS) may be used as a mutagen or ionizing radiation, such as x-ray, y-ray and fast-neutron radiation may be used as a mutagen. A worker skilled in the art would readily appreciate that the population may be subjected to targeted nucleotide exchange or region targeted mutagenesis. A worker skilled in the art would further appreciate that transposable elements can act as mutagens.

In certain embodiments of the invention, the population is a population of plants mutagenized with EMS or progeny thereof.

In certain other embodiments, the population is a population of Solanum lycopersicum mutagenized with EMS or progeny thereof.

In other embodiments, the population is a population of Capsicum annuum mutagenized with EMS or progeny thereof.

In other embodiments, the population may have been genetically engineered. A worker skilled in the art would readily appreciate methodologies for genetically engineering a population. Exemplary, non-limiting, methods include methods which utilize artificial constructs, methods of site specific mutagenesis through the use of designer enzyme systems (such as zinc-finger nucleases, transcription activator-like effector nucleases, meganucleases and nuclease based on CRISPR/Cas system) or constructs expressing the enzymes.
Method:

The present invention provides a method of identification of a mutation(s) in one or more target sequences in a population. The method comprises (a) pooling genomic DNA isolated from each member of the population in one or more dimensions; (b) amplifying the one or more target sequence(s) in the pooled genomic DNA; (c) sequencing the amplified products or obtaining the sequence reads for the amplified products; and (d) identifying the mutation(s) based on alignment-free sequence analysis of sequencing data. The methods optionally further comprise (e) identifying individual member(s) of the population comprising the one or more identified mutations in the target sequences. Optionally, the amplification products of step (b) are pooled prior to sequencing the amplified products. Optionally, for step (c), sequencing is by pair-end sequencing and further comprises merging the paired-end reads into composite read(s).

In specific embodiments, the invention provides a method for isolation of a member of a population which has one or more mutation(s) in one or more target sequence(s) in a population, comprising the steps of:
   (a) pooling genomic DNA isolated from each member of the population in one or more dimensions;
   (b) amplifying the one or more target sequence(s) in the pooled genomic DNA;
   (c) sequencing the amplified products to produce sequence read(s) for the amplified products;
   (d) identifying the mutation(s) based on k-mer analysis of the sequence read(s) of (c); wherein said k-mer analysis comprises
      (i) decomposing said sequence read(s) into k-mers;
      (ii) determining the number of occurrences of each of said k-mers from said decomposed sequencing read(s);
      (iii) determining a wild-type count and a mutant count for the target sequence k-mers using reference sequence(s) to identify all possible k-mers containing a particular base of the reference or target sequence, wherein, for each base in said reference sequence(s), said wild-type count is determined by determining frequency of all k-mers identified from said reference sequence(s) which include said base in said target sequence k-mers from said decomposed sequencing read(s);

wherein, for each base in said reference sequence(s), said mutant count is determined by changing said base in said reference sequence(s) to a different base to produce an altered reference sequence(s), identifying all k-mers containing the changed base, and determining frequency of said k-mers containing the changed base in said target sequence k-mers from said decomposed sequencing read(s);

(iv) identifying a mutation of said base in the target sequence(s); wherein a ratio of mutant count to wild-type count for said base that is significantly different than the ratio of mutant to wild-type counts for all other bases in said target sequence(s) is indicative of a mutation of said base in said target sequence(s); and (e) identifying individual member(s) of the population comprising the one or more identified mutation(s) in the target sequences.

Step (a): Pooling Genomic DNA Isolated from each Member of the Population in one or more Dimensions.

Methods of isolation of genomic DNA are known in the art. A worker skilled in the art would readily appreciate that the quality of the genomic DNA may impact the screening methodology and, as such, protocols which produce high quality genomic DNA with minimal contamination are preferable. In addition, a worker skilled in the art would readily appreciate that kits for isolation of genomic DNA are commercially available (for example PURELINK® Genomic Kit from Invitrogen or WIZARD® Genomic DNA Purification Kit from Promega).

Equimolar amounts of genomic DNA from each sample is used in one or more pools. Pooling of the isolated genomic DNA may be in one or more dimensions (i.e. unidimensional or multidimensional pooling). For unidimensional pooling each member of the population is represented once (i.e. in a single pool). For bidimensional pooling, each member of the population is represented twice (i.e. in two pools). For tridimensional pooling, each member of the population is represented three times (i.e. in three pools). Appropriate pooling strategies are known in the art (see, for example, Tsai et al., *Plant Physiology* 156:1257-1268). A worker skilled in the art would be aware of appropriate methods for identifying each pool in multidimensional pooling approaches (such methods may include tags or barcodes).

In one embodiment, equimolar amounts of genomic DNA from each well of a 96 well plate are pooled to create a pool plate. In another embodiment, equimolar amounts of genomic DNA from each well of a 384 well plate are pooled to create a pool plate. In embodiments in which unidimemsional pooling is used, each member of the population is represented once (i.e. a single pool plate). In embodiments in which bidimensional pooling is used, each member of the population is represented twice (i.e. in a row pool and a column pool). In embodiments in which tridimensional pooling is used, each member is represented three times (i.e. in a row pool, a column pool, and a plate pool).

A worker skilled in the art would readily appreciate that the amount of DNA from each sample will be dependent upon how many amplicons are needed. In certain embodiments, in order to reduce the impact of early stage DNA polymerase errors, at least 30 diploid genome copies of each individual in a well are used in a single PCR reaction.

In certain embodiments, greater than 50 genome copies from each individual in a well are pooled. A worker skilled in the art could readily determine the amount of DNA. For example, for petunia, at least 40 genome copies of each individual plant is ~20 ng. For tomato at least 25 genome copies are present in 50 ng of DNA extracted from 6×384 individuals. For pepper at least 6 genome copies are present in 50 ng of DNA extracted from 6×384 individuals. To further reduce the impacts of PCR errors replicate PCR reactions may be performed.

Step (b): Amplifying the one or more Target Sequence(s) in the Pooled Genomic DNA.

For each pool, the pooled genomic DNA is used as a template for polymerase chain reactions (PCR) which produce amplicons for one or more target sequence(s). Each PCR reaction preferentially amplifies a single region in the target sequence. In order to reduce the number of DNA polymerase errors propagated through the PCR, multiple PCR reactions using DNA from the pool may be performed and then combined. Optionally, the PCR reactions are purified (for example, by column purification) prior to combining. In certain embodiments, 3 to 12 PCR reactions are performed using DNA from the pool and then combined together. In certain embodiments, 5 PCR reactions are performed using DNA from the pool and combined together. A worker skilled in the art would readily appreciate that DNA polymerase errors may also be minimized by use of a high-fidelity enzyme such as Kapa Taq (Kapa Biosystems), Platinum Taq (Invitrogen), PFUUltra (Agilent Technologies) or Phusion (New England Biolabs).

A worker skilled in the art would readily appreciate methods for determining if the PCR reaction was successful and the amount of DNA produced. In addition, a worker skilled in the art would readily appreciate methods for concentrating and cleaning a PCR sample.

A worker skilled in the art would readily appreciate that not all commercial DNA polymerases are able to polymerize the same length of amplicon and not all regions of DNA are able to be amplified with the same efficiencies. Primers to amplify regions of interest are chosen to maximize the length of target sequence amplified and produce a robust single band when viewed on an agarose gel. Typically, the size of the amplicon ranges from 1000 bp to greater than 6500 bp depending on the length of the region one is amplifying and the DNA polymerase used. In cases where the region of interest is larger than what can be produced in a single PCR product, the region of interest is amplified as two or more smaller PCR products that overlap. At least 200 bp of overlap is generated between amplicons. This is done to compensate for the low sequencing coverage often found at the 5' and 3' extremes of the product being sequenced. A worker skilled in the art would appreciate that the PCR conditions used will be dependent on the DNA polymerase used, the primers selected and the quality of the PCR template DNA.

Optionally, the Amplification Products of Step (b) are Pooled Prior to Sequencing the Amplified Products.

The amplification products of step (b) may be optionally combined in equimolar amounts prior to sequencing. For example, equimolar amounts of DNA from four 96-well amplicon pools targeting the same region of the target sequence may be combined to produce a 384-well amplicon pool to one region of the target sequence. Alternatively, a single 384-well plate is used to produce the 384-well pool. Equimolar amounts of a number of these 384-well amplicon pools targeting different regions of the target sequence or different target sequences may then be combined. In one embodiment, eight 384-well amplicon pools are combined. The number of 384 well plates depends on the population size. In certain embodiments, the number of 384 well plates range from 1 to 15 384 well amplicon pools.

In certain embodiments, a sufficient number of amplicon pools targeting different regions within the target sequence are combined such that the complete target sequence is represented in the library pool. In other embodiments a sufficient number of amplicon pools targeting different target sequences are combined to produce the library pool.

In certain embodiments, equimolar amounts of four 96-well amplicon pools targeting a single region of the target sequence (or single target sequence) are combined to produce a 384-well amplicon pool. In other embodiments, a single 384-well plate is used to produce the 384-well amplicon pool. Equimolar amounts of multiple 384-well amplicon pools targeting different regions of the target sequence or different target sequences are then combined to produce a library pool. In certain embodiments, eight 384-well amplicon pools targeting overlapping regions of the target sequence are combined.

A worker skilled in the art would readily appreciate how to concentrate and clean the 384-well amplicon pool prior to combining multiple pools. Methods of preparing a sample for sequencing are known in the art and kits are commercially available (for example, next generation sequencing technology from Illumina). Depending on the sequencing technology used, the methods of preparation a sample for sequencing may include, for example, random fragmentation of the DNA sample and 5' and 3' adapter ligation prior to the PCR amplification. In certain embodiments, the average insert size of the sequencing library is set to the read length of the sequencing run so that the overlap between the forward and reverse reads is maximized. In certain embodiments, the average insert size of the sequencing library is set to 100 base pairs.

Step (c): Sequencing the Amplified Products or Obtaining the Sequence Reads for the Amplified Products.

Sequencing may be conducted by any means known in the art. In certain embodiments, sequencing is performed using high-throughput sequencing methods. Such methods are known in the art and include, for example, next generation sequencing technology such as Illumina's sequencing-by-synthesis or ThermoFisher Scientific's semi-conductor sequencing. In certain embodiments, the sequencing is conducted by a third party.

Optionally, for Step (c), Sequencing is by Pair-End Sequencing and Further Comprises Merging the Paired-End Reads into Composite Read(s).

In certain embodiments, sequencing is by paired-end sequencing. Forward and reverse reads are optionally combined into a single composite read. Base calls with an error likelihood of >1/10,000 or 1/100,000 are removed or masked. In certain embodiments, the paired-end sequencing is conducted by a third party and the paired-end sequencing data is obtained from the third party.

A worker skilled in the art would readily appreciate that a forward and reverse read-pair are independent sequencing reactions over the same template molecule. Such a worker would further appreciate that when base calls from aligned reads agree in both the forward and reverse directions the confidence that the base is called correctly increases. Rodrigue et al. (PLoS One 4:34761) demonstrated that combining the forward and reverse read-pairs from an Illumina paired-end sequencing run reduces the sequencing error-rate by 2-orders of magnitude. With an error rate of 1/100,000 or better, DNA samples from thousands of individuals can be sequenced at once without losing mutations in a sea of noise.

A worker skilled in the art would readily appreciate that there is software available, such as SHERA ((Rodrigue et al, PLoS One 4:34761) or PEAR (Zhang et al., Bioinformatics 30(5): 614-620) which may be used to produce composite reads from the paired-end reads. Alternatives to SHERA and PEAR include COPE (Liu et al, Bioinformatics 28(22): 2870-2874, FLASH (Magoč and Salzberg, Bioinformatics 27(21): 2957-2963), and PANDASeq (Masella et al, BMC Bioinformatics 13:31).

Step (d) Identifying the Mutation(s) Based on Alignment-Free Sequence Analysis of Sequencing Data.

Sequences may be analyzed and mutation(s) identified using either alignment based approaches or alignment-free approaches. In the present invention, sequences are analyzed using alignment-free methods. Various alignment-free methods of sequence analysis are known in the art and include but are not limited to methods based on k-mer frequency. A worker skilled in the art would readily appreciate that k-mers (also referred to as kmers) are short, overlapping fragments generated from a longer sequence. The size of the fragments can be of any length equal or shorter than the length of the sequencing read they are generated from. In one embodiment, the k-mers are about 15 to 31 nucleotides. In one embodiment, the k-mers are about 15 nucleotides. In a specific embodiment the k-mers are 17 nucleotides in length.

A worker skilled in the art would readily appreciate that a sequencing read from the pool of genomic DNA isolated from members of a population will include (1) wild type sequences and (2) non-wild type sequences. The non-wild type sequences may be the result of actual mutations or sequencing errors.

A reference sequence may be used to identify k-mers resulting from wild type sequences in the sequencing reads and to determine a wild type count for each base. In certain embodiments, the wild-type count is determined by determining frequency of all k-mers identified from the reference sequence(s) which include the base in the target sequence k-mers from the decomposed sequencing read(s).

The reference sequence may also be used to generate altered sequences (i.e. non-wild type sequences) and k-mers resulting from non-wild type sequences (i.e. either mutant or sequencing errors) in the sequencing reads and to determine a mutant count (i.e. non-wild type count) for each base. In particular, in certain embodiments, for each base in the reference sequence(s), the mutant count is determined by changing the base in the reference sequence(s) to a different base to produce an altered reference sequence(s), identifying all k-mers containing the changed base, and determining frequency of the k-mers containing the changed base in the target sequence k-mers from the decomposed sequencing read(s). This process may be repeated for each position of the reference sequence and different bases may be used to produce the altered reference sequence(s).

An actual mutation (i.e. not a sequencing error) in the target sequence(s) is identified (i.e. distinguished from non-wild type bases resulting from sequencing errors) by comparing the ratio of the mutant count to wild-type count for the base to the ratio of the mutant count to wild-type count for all other bases in the target sequence(s). A ratio that is significantly different than the ratio of mutant to wild-type counts for all other bases in the target sequence(s) is indicative of an actual mutation of said base in the target sequence(s)

A worker skilled in the art would readily appreciate appropriate reference sequences. For example, a reference sequences may be the known sequence including but not limited to sequences from publicly available databases including but not limited to International Nucleotide Sequence Database, DNA Data Bank of Japan, EMBL, GenBank or publicly available genome databases such as Plant GDB. Reference sequences may also be identified from the sequenced genomes of various organisms including but not limited to *Arabidopsis thaliana*, tomato, pepper, cucumber, melon, grape vine, apple, peach, eggplant, wheat, barley, maize, rice, potato, sweet potato, and rose. A reference sequence could also be determined using the sequencing information from the PCR products of the amplicons.

In certain embodiments, the k-mer analysis comprises (i) decomposing said sequence read(s) of the target sequence(s) into k-mers; (ii) determining the number of occurrences of each of the k-mers from the decomposed sequencing read(s) of the target sequence(s); (iii) determining a wild-type count and a mutant count for the target sequence k-mers using reference sequence(s) to identify all possible k-mers containing a particular base of the reference or target sequence. For each base in the reference sequence(s), the wild-type count is determined by determining frequency of all k-mers identified from the reference sequence(s) which include the base in the target sequence k-mers from the decomposed sequencing read(s). For each base in the reference sequence(s), the mutant count is determined by changing the base in the reference sequence(s) to a different base to produce an altered reference sequence(s), identifying all k-mers containing the changed base, and determining frequency of the k-mers containing the changed base in the target sequence k-mers from the decomposed sequencing read(s). For each base, a mutation (i.e. not a sequencing error) in the the target sequence(s) is identified by comparing the ratio of the mutant count to wild-type count for the base to the ratio of the mutant count to wild-type count for all other bases in the target sequence(s). A ratio that is significantly different than the ratio of mutant to wild-type counts for all other bases in the target sequence(s) is indicative of a mutation of said base in the target sequence(s).

Optional Step (e) Identifying Individual Member(s) of the Population Comprising the one or more Identified Mutations in the Target Sequences.

In certain embodiments, the method further comprises identifying individual member(s) of the population comprising the one or more identified mutations in the target sequences. Various methods may be used to identify individual member(s) comprising the mutation(s) of interest. For example, these methods may include High Resolution Melting, enzyme based methods (such as digestion of mismatch sites in heteroduplexes with CEL1 endonuclease), hybridization-based approaches, sequencing approaches and, in methods, which utilize multidimensional pooling and barcoding (such as tridimensional pooling) identification based on the barcode.

In one embodiment, High Resolution Melting (HRM) is used to identify member(s) of the population comprising the one or more identified mutations in the one or more target sequence(s). Methods of HRM are known to a worker skilled in the art. See, for example, Erali and Witter (Methods 50(4):250-261). In particular, HRM may be conducted utilizing primers which flank the identified mutation alone or in combination with a 3' block nucleotide probe (such as LUNAPROBE™ (as described by Idaho Technology) and the genomic DNA of the individuals of the population, which may or may not be pooled.

In certain embodiments, once the presence of a mutation in a population has been detected, the individual DNA sample containing the mutation is identified using HRM (De Koeyer et al, Molecular Breeding 25: 67-90). In some embodiments, PCR primers flanking the mutation of interest are created and used to amplify a product containing the mutation site in each of the DNA samples from the 384 well pools where the mutation of interest was identified. The PCR primers can be designed such that the amplicon size is less than 75 bp and no naturally occurring heterozygous DNA positions. In certain embodiments, the single DNA sample containing the mutation is identified through melt curve analysis. For example, a 384 well LIGHTSCANNER® (Idaho Technology) and LCGREEN® Plus HRM dye may be used in the melt curve analysis. Optionally, the presence of the mutation may be confirmed. In certain embodiments, to confirm the mutation, the seed collected from plants contributing DNA to that sample are planted and grown. Tissues are collected from these plants and their DNA analyzed using sequencing so that individual plants with the mutation are identified.

Optionally, the presence of the mutation may be confirmed in the individual identified through other SNP detection methods.

Phenotypic Analysis

Phenotypic evaluation of plants may be performed to determine if the mutations of interest have an effect on the performance of the plant under various conditions. Types of phenotypic analysis include, but are not limited to, evaluating drought stress responses, low temperature growth, heat tolerance, pathogen resistance, yield, change in morphology (including but not limited to plant height, size and/or colour of leaf, seed and/or flower), modification in life span and/or disease susceptibility.

Kits

Kits comprising one or more of reagents necessary for the methods set forth therein. For example, the kits may include any of one or more primers, probes, DNA polymerase and other reagents and instructions for use.

To gain a better understanding of the invention described herein, the following examples are set forth. It will be understood that these examples are intended to describe illustrative embodiments of the invention and are not intended to limit the scope of the invention in any way.

EXAMPLE 1

In one embodiment of the present invention, the method of screening a population comprising a mutation in one or more target sequences comprises the following steps:
1. Creation of stoichiometrically balanced amplicon pools for sequencing
   a) Plate pooling—DNA has been extracted from each individual in our EMS population and arrayed into 96-well microtitre plates. For each sample in a 96-well plate equimolar amounts were aliquoted into a single tube. These are the plate pools.
   b) PCR of amplicons—Design PCR primers that produce PCR product for the DNA region(s) under investigation. For each amplicon multiple PCR reactions using DNA from a plate pool as template were performed. This was done to reduce the overall concentration of DNA polymerase errors propagated through the PCR for the amplicon. Replicate PCRs were pooled into a single tubed, visualized on an agarose gel, and quantified. This was done for each plate pool. These samples are the amplicon pools.

c) Creating 384-well plate pools—Equimolar amounts of 4 amplicon pools were pooled into a single tube. These are the 384-well amplicon pools. This was done to have all individuals represented on our 384-well HRM plates in a single pool. This reduces the amount of work needed during the genotyping phase of the mutant identification/verification. Each 384-well amplicon pool was run through a PCR cleanup column to both clean and concentrate the samples. DNA from the column was eluted in the smallest water volume that is reasonable. The clean amplicon pools were quantified.

d) Producing the library pools to sequence—All of the amplicons that used the same 4 96-well plate pools were combined into a single library pool, taking care to aliquot amplicons in equimolar amounts. Each library pool was sequenced on an Illumina sequencing instrument.

2. Identification of Mutation a) Merging paired-end (PE) reads—The PE reads represent independent sequencing reactions from the two ends of the same template. When the template approaches the same length as the sequencing reads the paired-ends overlap. These reads can be merged into a single composite read where we have greater certainty in the base calls. This dramatically reduces errors due to miscalling during the sequencing reaction. The software PEAR was used to create the composite reads.

b) Create k-mer table—Merged reads were decomposed into short, overlapping fragments called kmers. The size of the fragments can be of any length but typically 15 to 31 work well. Selection of a k-mer size can be done empirically or through examination of the reference sequence. An optimal k-mer length derived from the reference sequences is a length where all of the k-mers generated from the reference sequence are at least a Hamming distance of 1, preferable 2 from each other. The number of times each k-mer was present in the high quality sequencing data was recorded in a lookup table. The software Jellyfish was used to create the lookup table. After building the lookup table, the reference sequence(s) were traversed one base at a time. For each base all of the reference sequence k-mers were determined and the reverse complement of those kmers that include it and average how many times those k-mers were found in the sequencing data (from the kmer lookup table). This gives a measure of wild-type 'coverage' (i.e. wild-type count). Then, one at a time change each G in the reference to A or C to T and count how many times all of the kmers including the changed base are present in the sequencing data (from the lookup table. The average of this value gives a measure of mutation (i.e. mutant count). This step can be expanded to change each base of the reference to each of the remaining 3 nucleotides.

c) Mutation selection—An actual mutation (i.e. not a sequencing error) in the target sequence(s) was identified (i.e. distinguished from non-wild type bases resulting from sequencing errors) by comparing the ratio of the mutant count to wild-type count for the base to the ratio of the mutant count to wild-type count for all other bases in the target sequence(s). A ratio that is significantly different than the ratio of mutant to wild-type counts for all other bases in the target sequence(s) is indicative of an actual mutation of said base in the target sequence(s).

3. Identification of the member of population comprising the mutation—HRM was used to genotype the population for plants that contain mutations of interested identified in the previous step. The breadth of searches is limited by identifying the 384-libraries containing the mutation.

EXAMPLE 2

In the following example, six genes were PCR amplified from a tomato EMS population from 8 pools consisting of DNA. Each pool was comprised of DNA from 384 individuals. For each of the 8 pools the three amplicons were mixed in equimolar amounts. The 8 amplicon pools were then used as template to construct Illumina Nextera libraries and were sequenced on an Illumina MiSeq instrument using a version 3 600-cycle reaction kit. Paired-end reads were merged using the software PEAR and the resulting merged and un-merged reads were used for further analysis.

Using the software Jellyfish (Marcais et al, 2011) and the output from PEAR, a k-mer size of 15 was selected and a table of each k-mer that appeared in the sequencing data was created and the number of times that k-mer was encountered. Only k-mers with all bases having a quality score >30 were used.

Then, for each DNA base in the reference sequences all of the 15-mers that were possible that included that position were generated. Using these 15-mers and the table generated with Jellyfish the total count for all 15-mers incorporating the current position in the sequencing data were summed and divided by the number of intersecting 15-mers. This value represented the 'wild-type' count for this position. The wild-type identity of that base was then changed ('mutated') to each of the other three DNA bases. For each of these other three bases the same procedure as outlined above was used to determine the total count for all intersecting 15-mers for the 'mutated' bases that were generated using the changed sequence. The highest of these values represented the 'mutant count' for that position of the reference. A normalized mutant count for each position was calculated and the values across the 8 libraries were compared. Libraries with a ratio differing significantly from the others indicated a member of the population pool from which the library was produced comprises a mutation at that position. In this example the ratio used was the quotient of the mutant count (mt) to the wildtype count (wt) for the library with the greatest mutant count at that position divided by the quotient of the sum of the mutant counts from all other libraries at that position (other-mt) to the wildtype counts from all other libraries at that position (other-wt) [(mt/wt)/(other-mt/other-wt)]. A Poisson distribution fit this data and was used to estimate p-values for each of these ratios. A p-value cut-off was empirically assigned and used as a parameter in selecting which putative mutations were real. The individual member of the population containing the identified mutation was identified using a high resolution DNA melting. Using this technique, individual members comprising a mutation listed below was identified.

TABLE 1

Mutations confirmed. Using the outlined methodology 13 mutations previously identified in these genes using an alternative approach

| Gene | Reference Position | Mutation | Ratio | P-value |
|---|---|---|---|---|
| A1 | 6049 | G -> A | 41.34 | 4.26e-15 |
| A2 | 3075 | G -> A | 95.05 | 1.19e-61 |
| A2 | 3405 | G -> A | 114.43 | 1.05e-81 |
| A2 | 4056 | G -> A | 61.01 | 4.31e-30 |
| A3 | 2326 | G -> A | 95.72 | 1.19e-61 |
| A3 | 3509 | G -> A | 22.13 | 1.11e-04 |
| A4 | 1451 | G -> A | 46.03 | 1.59e-18 |
| A5 | 601 | G -> A | 64.92 | 1.32e-32 |
| A5 | 1153 | G -> A | 55.53 | 2.96e-25 |
| A5 | 1353 | G -> A | 15.98 | 2.90e-02 |
| A6 | 865 | G -> A | 88.91 | 1.17e-54 |
| A6 | 869 | C -> T | 37.02 | 1.56e-12 |
| A6 | 8528 | G -> A | 38.75 | 3.70e-13 |

TABLE 2

Mutations confirmed. Using the outlined methodology all 24 mutations previously identified in these genes using an alternative approach

| Gene | Reference Position | Mutation | Ratio | P-value |
|---|---|---|---|---|
| B | 1140 | G -> A | 199.24 | 1.32e-185 |
| D | 687 | G -> A | 104.12 | 6.72e-71 |
| B | 3204 | C -> T | 79.28 | 5.80e-46 |
| B | 3070 | C -> T | 95.47 | 1.37e-61 |
| A | 4589 | C -> T | 116.16 | 7.97e-84 |
| A | 18659 | G -> A | 69.59 | 7.00e-37 |
| D | 1591 | C -> T | 48.54 | 6.20e-20 |
| A | 1311 | G -> A | 121.05 | 2.27e-89 |
| D | 1255 | C -> T | 75.10 | 2.91e-42 |
| B | 3744 | G -> A | 74.25 | 2.38e-41 |
| A | 5667 | G -> A | 47.17 | 3.27e-19 |
| B | 6096 | G -> A | 58.61 | 1.32e-27 |
| A | 18214 | G -> A | 113.13 | 1.53e-80 |
| A | 5566 | G -> A | 86.64 | 1.21e-52 |
| D | 1063 | C -> T | 32.01 | 1.45e-09 |
| B | 7948 | C -> T | 41.20 | 4.50e-15 |
| D | 825 | G -> A | 39.78 | 9.00e-14 |
| A | 1061 | C -> T | 38.46 | 3.88e-13 |
| A | 19666 | C -> T | 34.07 | 1.04e-10 |
| B | 3421 | C -> T | 47.78 | 3.27e-19 |
| A | 3009 | C -> T | 49.63 | 1.15e-20 |
| B | 7885 | C -> T | 30.95 | 1.80e-08 |
| D | 1228 | C -> T | 28.03 | 1.97e-07 |
| D | 1065 | G -> A | 34.67 | 1.04e-10 |

EXAMPLE 3

In the following example 4 amplicons from 3 genes were PCR amplified from a pepper EMS population from 9 pools consisting of DNA. Each pool was comprised of DNA from 384 individuals. For each of the 9 pools the four amplicons where mixed in equimolar amounts. The 9 amplicon pools were used as template to construct Illumina Nextera libraries and were sequenced on an Illumina MiSeq instrument using a version 3 600-cycle reaction kit. Using the software Jellyfish (Marcais et al, 2011) with a k-mer size of 17 a table of each k-mer that appeared in the sequencing data was created and the number of times that k-mer was encountered. Then, for each DNA base in the reference sequences all of the 17-mers that were possible which included that position were generated. Using these 17-mers and the table generated with Jellyfish the total count for all 17-mers incorporating the current position in the sequencing data were summed and divided by the number of intersecting 17-mers. This value represented the 'wild-type' count for this position. The wild-type identify of that base was then changed ('mutated') to each of the other three DNA bases. For each of these other three bases the same procedure as outlined above was used to determine the total count for all intersecting 17-mers for the 'mutated' bases that were generated using the changed sequence. The highest of these values represented the 'mutant count' for that position of the reference. A normalized mutant count for each position was calculated and the values across the 9 libraries were compared. Libraries with a ratio differing significantly from the others indicated member of the population pool from which the library was produced comprises a mutation at that position. In this example the ratio used was the quotient of the mutant count (mt) to the wildtype count (wt) for the library with the greatest mutant count at that position divided by the quotient of the sum of the mutant counts from all other libraries at that position (other-mt) to the wildtype counts from all other libraries at that position (other-wt) [(mt/wt)/(other-mt/other-wt)]. A Poisson distribution fit this data and was used to estimate p-values for each of these ratios. A p-value cut-off was empirically assigned and used as a parameter in selecting which putative mutations were real. The individual member of the population containing the identified mutation was identified using HRM method. Using this technique individual members comprising a mutation listed below were identified.

EXAMPLE 4

In the following example the alignment-free methodology of mutant discovery of the invention was applied to a published dataset for TILLING-by-sequencing in a rice population (Tsai et al, Plant Physiology 156(3):1257-1268). From the publication, the DNA from 768 rice plants was aliquoted in a three-dimensional pooling strategy; 16 row pools of 48 individuals each, 16 column pools of 48 individuals each, and 12 dimensional pools of 64 individuals each. We attempted to recapitulate the nucleotide transition results for one of the gene targets defined in the original publication. Forty-eight libraries consisting of 247,895,886 Illumina single-end 79 base-pair reads were downloaded from the Genbank Short Read Archive under the identifier 'SRP006801'. Using the software Jellyfish (Marcais et al, 2011) with a k-mer size of 17 a table of each k-mer that appeared in the sequencing data was created and the number of times that kmer was encountered. Any k-mers with a count <2 where discarded from the analysis as they represented sequencing errors and not true mutation sequence. Then, for each DNA base in the reference sequence, OS01G63510, all of the 17-mers that were possible which included that position were generated. Using these 17-mers and the table generated with Jellyfish the total count for all 17-mers incorporating the current position from the sequencing data were summed and divided by the number of intersecting 17-mers. This value represented the 'wild-type' count for this position. The wild-type identify of that base was then changed ('mutated') to each of the other three DNA bases. For each of these other three bases the same procedure as outlined above were used to determine the total count for all intersecting 17-mers for the 'mutated' bases that were generated using the changed sequence. The highest of these values represented the 'mutant count' for that position of the reference.

According to Tsai et al., a real mutation should generate significant mutant base counts in exactly 1 row library, 1 plate library, and 1 dimensional library. This is exactly what was found for the transition mutations at position 530 and 777 of the reference sequence were we trying to identify. Each of these positions had only 3 non-zero mutant allele counts with one non-zero count in each of the row, plate, and dimensional pools. This analysis completed in under an hour.

CITATIONS

De Koeyer, D. L., Douglass, K., Murphy, A. M., Whitney, S., Nolan, L., Song, Y., and De Jong, W. S. (2010). "*Application of high-resolution DNA melting for genotyping and variant scanning of diploid and autotetraploid potato.*", Molecular Breeding, 25(1), pp. 67-90.

Erali M, Wittwer C T. High Resolution Melting Analysis for Gene Scanning.Methods (San Diego, Calif.). 2010; 50(4):250-261.

Fitzpatrick T B, Basset G J, Borel P, Carrari F, DellaPenna D, Fraser P D, Hellmann H, Osorio S, Rothan C, Valpuesta V, Caris-Veyrat C, Fernie A R. Vitamin deficiencies in humans: can plant science help? Plant Cell. 2012 February; 24(2):395-414.

Forster, B. P. (2001) Mutation genetics of salt tolerance in barley: A assessment of Golden Promise and other semi-dwarf mutants. Euphytica 120(3): 317-328.

Gady A L, Hermans F W, Van de Wal M H, van Loo E N, Visser R G, Bachem C W. Implementation of two high through-put techniques in a novel application: detecting point mutations in large EMS mutated plant populations. Plant Methods. 2009 Oct. 7; 5:13.

Koornneef, M., Dellaert, L. W., and van der Veen, J. H. (1982) EMS-and radiation-induced mutation frequencies at individual loci in *Arabidopsis thaliana* (L) Heynh. Mutat Res 93:109-123.

Liu B, et al. COPE: an accurate k-mer-based pair-end reads connection tool to facilitate genome assembly. Bioinformatics. 2012; 28:2870-2874.

Magoč T, Salzberg S L. FLASH: fast length adjustment of short reads to improve genome assemblies. Bioinformatics. 2011; 27:2957-2963.

Marçais G, Kingsford C. A fast, lock-free approach for efficient parallel counting of occurrences of k-mers. Bioinformatics. 2011 Mar. 15; 27(6):764-70.

Masella A P, et al. PANDAseq: paired-end assembler for Illumina sequences. BMC Bioinformatics. 2012; 13:31.

McCallum, C., Comai, L., Greene, E. A., and Henikof, S. (2000) Targeting induced local lesions in genomes (TILLING) for plant functional genomics. Plant Physiol 123(2): 439-442.

Minoche, A. E., Dohm, J. C., Himmelbauer, H. (2011). Evaluation of genomic high-throughput sequencing data generated on Illumina HiSeq and genome analyzer systems. Genome Biology. 12: R112.

Missirian V, Comai L, Filkov V. Statistical mutation calling from sequenced overlapping DNA pools in TILLING experiments. BMC Bioinformatics. 2011 Jul. 14; 12:287.

Nordström K J, Albani M C, James G V, Gutjahr C, Hartwig B, Turck F, Paszkowski U, Coupland G, Schneeberger K. Mutation identification by direct comparison of whole-genome sequencing data from mutant and wild-type individuals using k-mers. Nat Biotechnol. 2013 April; 31(4): 325-30.

Rigola D, van Oeveren J, Janssen A, et al. High-Throughput Detection of Induced Mutations and Natural Variation Using KeyPoint™ Technology. Herrera-Estrella A, ed. PLoS ONE. 2009; 4(3):e4761.

Rodrigue S, Materna A C, Timberlake S C, Blackburn M C, Malmstrom R R, Alm E J, Chisholm S W. Unlocking short read sequencing for metagenomics. PLoS One. 2010 Jul. 28; 5(7):e11840

Sargent R G, Kim S, Gruenert D C. Oligo/polynucleotide-based gene modification: strategies and therapeutic potential. Oligonucleotides. 2011 March-April; 21(2):55-75.

Stadler, L. J. (1932) On the genetic nature of induced mutations in plants. Proc VI Congress of Genetics 1:274-294 (www.agris.fao.org).

Tsai, H., Howell, T., Nitcher, R., Missirian, V., Watson, B., Ngo, K. J., Lieberman, M., Fass, J., Uauy, C., Tran, R. K., Khan, A. A., Filkov, V., Tai, T. H., Dubcovsky, J., Comai, L. (2011). Discovery of rare mutations in populations: TILLING by sequencing. Plant Physiology. 156:1257-1268.

Wang, T. L., Uauy, C., Robson, F. and Till, B. (2012), TILLING in extremis. Plant Biotechnology Journal, 10: 761-772.

Zhang J, Kobert K, Flouri T, Stamatakis A. PEAR: a fast and accurate Illumina Paired-End read mergeR. Bioinformatics. 2014; 30(5):614-620.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. A method for identifying member(s) of a population comprising one or more mutation(s) in one or more target sequence(s), wherein each member of said population is distinct, said method comprising the steps of:
   (a) pooling genomic DNA isolated from each member of the population in one or more dimensions;
   (b) amplifying the one or more target sequence(s) in the pooled genomic DNA;
   (c) sequencing the amplified products to produce sequence read(s) for the amplified products;
   (d) identifying the one or more mutation(s) based on k-mer analysis of the sequence read(s) of (c);
   wherein said k-mer analysis comprises
      (i) decomposing said sequence read(s) into k-mers;
      (ii) determining the number of occurrences of each of said k-mers from said decomposed sequencing read(s);
      (iii) determining a wild-type count and a mutant count for the target sequence k-mers using reference sequence(s) to identify all possible k-mers containing a particular base of the reference or target sequence,
         wherein, for each base in said reference sequence(s), said wild-type count is determined by determining frequency of all k-mers identified from said reference sequence(s) which include said base in said target sequence(s) k-mers from said decomposed sequencing read(s);
         wherein, for each base in said reference sequence(s), said mutant count is determined by changing said base in said reference sequence(s) to a different base to produce an altered reference sequence(s), identifying all k-mers containing the changed base, and determining frequency of said k-mers containing the changed base in said target sequence k-mers from said decomposed sequencing read(s);

(iv) identifying a mutation of said base in the target sequence(s); wherein a ratio of mutant count to wild-type count for said base in said target sequence(s) that is significantly different than the ratio of mutant to wild-type counts for all other bases in said target sequence(s) is indicative of a mutation of said base in said target sequence(s); and (e) identifying individual member(s) of the population comprising the one or more identified mutation(s) in the target sequences.

2. The method of claim 1, wherein said sequencing is by pair-end sequencing and further comprises merging the paired-end reads into composite read(s).

3. The method of claim 1, wherein said step of amplifying comprises amplifying more than one sample of the pooled genomic DNA, and pooling amplification products from each sample to create pool(s) of amplification products.

4. The method of claim 1, wherein said sequencing is conducted by a third party.

5. The method of claim 1, wherein said population is mutagenized by mutation-inducing chemicals, ionizing radiation, targeted nucleotide exchange or region targeted mutagenesis.

6. The method of claim 1, wherein said identifying member(s) of the population comprising one or more of the identified mutations in the target sequence(s) is by high-resolution DNA melting (HRM).

7. The method of claim 1, further comprising, after the step of identifying individual member(s) of the population comprising the one or more identified mutations in the target sequences, conducting phenotypic analysis of said individual member(s) comprising the one or more identified mutations in the target sequences.

8. The method of claim 1, wherein said population is a population of plants.

9. The method of claim 8, wherein said population of plants comprises a grain crop, oilseed crop, fruit crop, vegetable crop, a biofuel crop, ornamental plants, flowering plants, annual plants, or perennial plants.

10. The method of claim 8, wherein said population of plants comprises plants selected from the group consisting of petunia, tomato, pepper, lettuce, potato, onion, carrot, broccoli, celery, pea, spinach, impatiens, cucumber, rose, sweet potato, fruit trees, eggplant, okra, corn, soybean, canola, wheat, oat, rice, soghum, cotton and barley.

* * * * *